United States Patent
Endlich et al.

(10) Patent No.: US 11,747,326 B2
(45) Date of Patent: Sep. 5, 2023

(54) DIAGNOSTIC TOOL TO DETERMINE PODOCYTE FOOT PROCESS EFFACEMENT

(71) Applicant: NIPOKA GmbH, Greifswald (DE)

(72) Inventors: Karlhans Endlich, Greifswald (DE); Nicole Endlich, Greifswald (DE); Florian Siegerist, Greifswald (DE)

(73) Assignee: NIPOKA GmbH, Greifswald (DE)

( * ) Notice: Subject to any disclaimer, the term of this patent is extended or adjusted under 35 U.S.C. 154(b) by 372 days.

(21) Appl. No.: 16/609,080

(22) PCT Filed: Apr. 26, 2018

(86) PCT No.: PCT/EP2018/060779
§ 371 (c)(1),
(2) Date: Oct. 28, 2019

(87) PCT Pub. No.: WO2018/197633
PCT Pub. Date: Nov. 1, 2018

(65) Prior Publication Data
US 2020/0049698 A1   Feb. 13, 2020

(30) Foreign Application Priority Data

Apr. 27, 2017 (EP) .................................. 17168506

(51) Int. Cl.
G01N 33/50 (2006.01)
G01N 1/30 (2006.01)
G01N 33/68 (2006.01)

(52) U.S. Cl.
CPC ........... *G01N 33/5091* (2013.01); *G01N 1/30* (2013.01); *G01N 33/6854* (2013.01); *G01N 2800/347* (2013.01)

(58) Field of Classification Search
CPC .. G01N 33/5091; G01N 1/30; G01N 33/6854; G01N 2800/347
See application file for complete search history.

(56) References Cited

U.S. PATENT DOCUMENTS

2005/0222027 A1* 10/2005 Chiang .............. A61K 38/1709
424/94.63

FOREIGN PATENT DOCUMENTS

| JP | 2009531327 A | 9/2009 |
| WO | 2007112280 A1 | 10/2007 |
| WO | 2008075173 A2 | 6/2008 |
| WO | 2010042202 A1 | 4/2010 |
| WO | 2010140024 A1 | 12/2010 |

OTHER PUBLICATIONS

Pullman (Optical Society of America (OSA) 2016 vol. 7, No. 2, total 10 pages). (Year: 2016).*
Unnersjo-Jess Kidney International 2016 89:243-247 (Year: 2016).*
International Search Report; European Patent Office; International Application No. PCT/EP2018/060779; dated Jun. 6, 2018; 4 pages.
Written Opinion of the International Searching Authority; European Patent Office; International Application No. PCT/EP2018/060779; dated Jun. 6, 2018; 9 pages.
Vinita Agrawal et al.; Reduced Podocin Expression in Minimal Change Disease and Focal Segmental Glomerulosclerosis is Related to the Level of Proteinuria; Clin Exp Nephrol; 2013; 8 pages; vol. 17.
Sven-Olof Bohman et al.; Foot Process Fusion and Glomerular Filtration Rate in Minimal Change Nephrotic Syndrome; Kidney International; 1984; 5 pages; vol. 25.
Jeroen K.J. Deegens et al.; Podocyte Foot Process Effacement as a Diagnostic Tool in Focal Segmental Glomerulosclerosis; Kidney International; 2008; 9 pages; vol. 74.
Agnes B. Fogo et al.; AJKD Atlas of Renal Pathology: Minimal Change Disease; Am J Kidney Dis.; 2015; 2 pages; vol. 66, No. 2.
Peter N. Furness et al.; Glomerular Expression of Nephrin is Decreased in Acquired Human Nephrotic Syndrome; Nephrology Dialysis Transplantation; 1999; 4 pages; vol. 14.
M.G.L. Gustafsson et al.; Surpassing the Lateral Resolution Limit by a Factor of Two Using Structured Illumination Microscopy; Journal of Microscopy; May 2000; 6 pages; vol. 198, Pt. 2.
Mats G.L. Gustafsson et al.; Three-Dimensional Resolution Doubling in Wide-Field Fluorescence Microscopy by Structured Illumination; Biophysical Journal; Jun. 2008; 14 pages; vol. 94.
M.A. Hladunewich et al.; Determinants of GFR Depression in Early Membranous Nephropathy; Am J Physiol Renal Physiol; Jan. 14, 2003; 9 pages; vol. 284.
Bo Huang et al.; Breaking the Diffraction Barrier: Super-Resolution Imaging of Cells; Cell; Dec. 23, 2010; 12 pages; vol. 143.
Sally M. Marshall; The Podocyte: A Potential Therapeutic Target in Diabetic Nephropathy?; Current Pharmaceutical Design; 2007; 8 pages; vol. 13.
Jaakko Patrakka et al.; Expression of Nephrin in Pediatric Kidney Diseases; J Am Soc Nephrol; 2001; 8 pages vol. 12.
Jaakko Patrakka et al.; The Number of Podocyte Slit Diaphragms is Decreased in Minimal Change Nephrotic Syndrome; Pediatric Research; 2002; 7 pages; vol. 52, No. 3.

(Continued)

*Primary Examiner* — Changhwa J Cheu
(74) *Attorney, Agent, or Firm* — Taft Stettinius & Hollister LLP (57) ABSTRACT

The present invention relates to a method for diagnosing or pre-diagnosing a disease associated with podocyte foot process effacement in a subject or for determining the risk of a subject to develop a disease associated with podocyte foot process effacement, said method comprising the steps of a) determining the length of the slit diaphragm (ISD) formed by podocyte foot processes in a specific area A in a renal tissue sample of said subject by super resolution light microscopy; b) comparing the length of the slit diaphragm (ISD) formed by podocyte foot processes in a specific area A as determined in step (a) with the length of the slit diaphragm (ISD) formed by podocyte foot processes in a comparable specific area A in a renal tissue sample of a subject who at the time of the sampling showed no clinical symptoms of a disease associated with podocyte foot process effacement, wherein a deviation indicates a disease associated with podocyte foot process effacement.

24 Claims, 4 Drawing Sheets

(56) References Cited

OTHER PUBLICATIONS

James M. Pullman et al.; Visualization of Podocyte Substructure with Structured Illumination Microscopy (SIM): A New Approach to Nephrotic Disease; Biomedical Optics Express 302; Feb. 2016; 10 pages; vol. 7, No. 2.
Johannes Schindelin et al.; Fiji: An Open-Source Platform for Biological-Image Analysis; Nature Methods; Jul. 2012; 7 pages; vol. 9, No. 7.
Oliver Smithies; Why the Kidney Glomerulus Does Not Clog: A Gel Permeation/Diffusion Hypothesis of Renal Function; PNAS; Apr. 1, 2003; 6 pages; vol. 100, No. 7.
Carsten Steger; An Unbiased Detector of Curvilinear Structures; IEEE Transactions on Pattern Analysis and Machine Intelligence; Feb. 1998; 13 pages; vol. 20, No. 2.
Hani Suleiman et al.; Nanoscale Protein Architecture of the Kidney Glomerular Basement Membrane; eLife Research Article; 2013; 18 pages; vol. 2.
Maija Suvanto et al.; Podocyte Proteins in Congenital and Minimal Change Nephrotic Syndrome; Clin Exp Nephrol; 2015; 8 pages; vol. 19.
David Unnersjo-Jess et al.; Super-Resolution Stimulated Emission Depletion Imaging of Slit Diaphragm Proteins in Optically Cleared Kidney Tissue; Kidney International; 2016; 5 pages; vol. 89.
Jose G. Van Den Berg et al.; Podocyte Foot Process Effacement is not Correlated with the Level of Proteinuria in Human Glomerulopathies; Kidney International; 2004; 6 pages; vol. 66.
"Acta Physiologica," Official Journal of the Federation of European Physiological Societies, vol. 219, Mar. 2017.
Korean Office Action, Korean Intellectual Property Office, Korean Application No. 10-2019-7034313, dated Jun. 15, 2022, 4 pages.
Hladunewich, M.A. et al., "Determinants of GFR depression in early membranous Nephropathy" Am J Physiol Renal Physiol, vol. 284, Jan. 14, 2003.
Lahdenkari, Anne-Tiina et al., "Podocytes Are Firmly Attached to Glomerular Basement Membrane in Kidneys with Heavy Proteinuria" Journal of the American Society of Nephrology—J Am Soc Nephrol, vol. 15, Mar. 2004.
Jeffersson, J.A. et al., "Proteinuria in diabetic kidney disease: A mechanistic Viewpoint" International Society of Nephrology—Kidney International, Apr. 16, 2008.
Toyoda, Masao et al., "Podocyte Detachment and Reduced Glomerular Capillary Endothelial Fenestration in Human Type 1 Diabetic Nephropathy" Diabetes, vol. 56, Aug. 2007.
Veron, Delma et al., "Overexpression of VEGF-A in podocytes of adult mice causes glomerular disease" Kidney International, vol. 77, Mar. 10, 2010.
Cybulsky, Andrey et al., "Experimental membranous nephropathy redux" Am J Physiol Renal Physiol, vol. 289, 2005 Podocyte cytoskeltal changes induced by antibody compl. p. 664-666.
Wilson, Tony, "Resolution and optical sectioning in the confocal microscope" Journal of Microscopy, vol. 244, 2011.
Ilgen, Peter et al., "STED Super-Resolution Microscopy of Clinical Paraffin-Embedded Human Rectal Cancer Tissue" Plos One, vol. 9, No. 7, Jul. 15, 2014.
Declaration of Prof. Dr. Nicole Endlich dated May 20, 2022.
Email dated Jan. 24, 2017.
Email dated Mar. 7, 2017.
European Summons to attend oral proceedings pursuant to Rule 115(1) EPC, European Patent Office, European Application No. 17168506.8, Jul. 22, 2022, 16 pages.
Siegerist et al., Super-resolution microscopy of the podocyte slit diaphragm, Post Session B, 2017; pp. 117-118, John Wiley & Sons Ltd.
Japanese Office Action, Japanese Patent Office, dated Mar. 1, 2022, Japanese Patent Application No. 2019-557788, 6 pages.
Israeli Office Action, Israel Patent Office, Israeli Application No. 270131, dated Dec. 14, 2022, 4 pages.
Japanese Office Action, Japan Patent Office, Japanese Application No. 2019-557788, dated Nov. 22, 2022, 7 pages.
Korean Decision to Grant, Korean Intellectual Property Office, Korean Application No. 10-2019-7034313, dated Dec. 27, 2022, 2 pages.

* cited by examiner

DIAGNOSTIC TOOL TO DETERMINE PODOCYTE FOOT PROCESS EFFACEMENT

CROSS-REFERENCE TO RELATED APPLICATIONS

This application is a U.S. National Phase of International PCT Application No. PCT/EP2018/060779 filed Apr. 26, 2018, which claims the benefit of European Patent Application Serial No. 17168506.8 filed Apr. 27, 2017, the contents of each application are incorporated herein by reference in their entirety.

The present invention relates to a method for diagnosing or pre-diagnosing a disease associated with podocyte foot process effacement in a subject or for determining the risk of a subject to develop a disease associated with podocyte foot process effacement, said method comprising the steps of (a) determining the length of the slit diaphragm ($l_{SD}$) formed by podocyte foot processes in a specific area A in a renal tissue sample of said subject by super resolution light microscopy; (b) comparing the length of the slit diaphragm ($l_{SD}$) formed by podocyte foot processes in a specific area A as determined in step (a) with the length of the slit diaphragm ($l_{SD}$) formed by podocyte foot processes in a comparable specific area A' in a renal tissue sample of a subject who at the time of the sampling showed no clinical symptoms of a disease associated with podocyte foot process effacement, wherein a deviation indicates a disease associated with podocyte foot process effacement.

For decades, the gold standard for the pathological assessment of kidney disease has been the light- and electron microscopic evaluation of stained kidney biopsies. Rapid histopathological investigation and diagnostics of these sectioned biopsies is a crucial step for the following treatment especially of nephrotic diseases like minimal change disease (MCD), diabetic nephropathy and focal segmental glomerulosclerosis (FSGS). In the case of MCD, classic routine histopathological assessment (H&E, PAS, Silverstain, Trichrome) and immunohistology (IgG, IgM, IgA, C3) does not lead to the diagnosis, as the only major pathologic feature that can be found is the effacement of podocyte foot processes[1]. Therefore, time-consuming transmission electron microscopic (TEM) preparation and evaluation is required. Podocyte foot process effacement is characteristic of glomerulopathies, for example, for proteinuric renal diseases. Glomerulopathies are a set of diseases affecting the glomeruli of the nephron, which is the basic structural and functional unit of the kidney.

As described by Ernst Abbe, the physically determined resolution limit of light microscopy is about 200 nm in the xy- and even bigger in the z-direction. Lately a growing variety of superresolution (SR) microscopy techniques like stochastic optical reconstruction microscopy (STORM), stimulated emission depletion microscopy (STED) and structured illumination microscopy (SIM) has been successfully developed to overcome this resolution limit[2].

In 2013, SR microscopy has been first presented to the renal research community by Suleiman and colleagues with a STORM study about the distribution of proteins within the murine and human glomerular basement membrane[3]. In 2016, Unnersjo-Jess and colleagues showed a STED approach to visualize the slit diaphragm (SD) in optically cleared kidney tissue[4].

Undoubtedly, STORM and STED offer exciting opportunities and a high resolution, but unfortunately, the pitfall of these techniques is their demanding sample preparation (tissue clearing, special fluorophores and special imaging buffers) and image acquisition. It is therefore hardly imaginable that these techniques will become part of routine diagnostics.

Currently commercially available microscopes with SIM overcome Abbes optical resolution limit at least two fold in all three directions resulting in an about 10-fold increase in voxel resolution[5,6]. SIM works by sequential illumination of a sample through a defined grate. In the different illumination steps, the grate is shifted and rotated, so that the illumination pattern of the grate interferes with the original pattern of the sample creating so called Moiré patterns. In a second step, this frequency mixed patterns are then demodulated by digital reconstruction of the dataset leading to an improved spatial resolution. In contrast to other SR techniques like STED and STORM, SIM works with standard fluorophores and labelling procedures, making it an exciting new tool without the need of time-consuming establishment of new protocols and is therefore a ready-to-use system.

For scientists focusing on glomerular biology, SIM is a very tempting tool as podocytes foot processes (FP) have a width of roughly 200 nm subdivided by a slit diaphragm (SD) of about 30 nm. Therefore these structures cannot be imaged by conventional light microscopy and only ultrastructural evaluation by electron microscopy is used to quantify changes on the level of foot processes.[7,8]

Podocytes are cells in the nephron's Bowman's capsule. The podocyte foot processes (aka podocyte foot projections, or podocyte pedicels) wrap around capillaries of the glomerulus and leave slits between them. Blood is filtered through these slits, each known as a filtration slit bridged by the slit diaphragm. One zipper-like protein that forms the slit diaphragm is nephrin, wherein spaces are present between the teeth of the zipper, big enough to allow sugar and water through, but too small to allow proteins through. Podocytes respond to stress and injury by undergoing tremendous changes in shape. Foot process effacement is the most prominent and, yet in some ways, the most enigmatic of those changes. It has long been known that the width of the effaced podocyte foot processes ($d_{FP}$) is inversely correlated with renal function in glomerulopathies, for example proteinuric renal diseases.

Since the discovery of the different proteins that compose the slit diaphragm (e.g. nephrin, NEPH1, podocin) and the subsequent development of specific antibodies, there have been attempts to use them as diagnostic markers for glomerular diseases.[9,12] Until today, no reliable marker has been found to diagnose or subdivide nephrotic diseases. Lately, it has been shown that SIM can resolve the SD using specific labelling of podocin.[13] However, the conventional diagnosis of podocyte FP effacement is still done by TEM, which is a time consuming method.

The technical problem underlying the present invention was therefor the provision of a new method for diagnosing or pre-diagnosing glomerulopathies, i.e. diseases associated with podocyte foot process effacement, which allows a faster diagnosis, i.e. requires less time than the conventional TEM method.

Surprisingly, it has been found that the length of the slit diaphragm ($l_{SD}$) formed by podocyte foot processes can be used for the diagnosis of podocyte foot processes effacement.

Therefore, the present invention relates to a method for diagnosing or pre-diagnosing a disease associated with podocyte foot process effacement in a subject or for determining the risk of a subject to develop a disease associated with podocyte foot process effacement, said method comprising the steps of a) determining the length of the slit diaphragm ($l_{SD}$) formed by podocyte foot processes in a specific area A in a renal tissue sample of said subject by super resolution light microscopy;

b) comparing the length of the slit diaphragm ($l_{SD}$) formed by podocyte foot processes in a specific area A as determined in step (a) with the length of the slit diaphragm ($l_{SD}$) formed by podocyte foot processes in a comparable specific area A' in a renal tissue sample of a subject who at the time of the sampling showed no clinical symptoms of a disease associated with podocyte foot process effacement (healthy subject), wherein a deviation indicates a disease associated with podocyte foot process effacement.

It has been surprisingly found that the length of the slit diaphragm ($l_{SD}$) is changed, especially decreased, in subjects having podocyte foot process effacement. In podocyte foot process effacement, the interdigitating of the podocyte foot processes decreases since the podocyte foot processes retract, which—besides a change in podocyte foot process width—also results in a change in the form of the SD, which is less meandering and thus shorter. Thus, the length of the slit diaphragm ($l_{SD}$) is an indicator for a disease associated with podocyte foot process effacement.

The expression "slit diaphragm" comprises areas where the podocyte foot processes have the normal cell-to-cell contact of a slit diaphragm. However, the expression, especially in case of diseases associated with podocyte foot effacement, also covers areas where the podocyte foot processes cell-to-cell contact is altered and they are in contact via other connections, for example, tight junctions, adherence junctions or gap junctions.

According to (b), the length of the slit diaphragm ($l_{SD}$) in a specific area A as determined in (a) can be compared with the length of the slit diaphragm ($l_{SD}$) formed by podocyte foot processes in a comparable specific area A' in a renal tissue sample of a healthy subject. The length of the slit diaphragm ($l_{SD}$) of a healthy subject used in (b) can also be a reference value from the literature (if known).

A renal tissue sample is preferably used in the form of a histopathological section, more preferably in the form of a histopathological section selected from the group consisting of paraffin section, frozen section, polymer embedded section, for example, LR white, and semithin section, more preferably histopathological paraffin sections are used. Directly after biopsies or prior to or directly after kidney removal, the renal tissue sample is preferably fixed in or by a suitable fixation medium comprising a fixation agent, more preferably a fixation solution comprising a fixation agent, in order to obtain a fixated renal tissue sample and to keep the tissue as unaffected as possible. The fixation is done by perfusion fixation or immersion fixation.

The fixation agent is preferably selected from the group consisting of alcohol, acetone, formaldehyde and combinations of two or more thereof. More preferably, the fixation agent comprises formaldehyde. The fixation solution preferably comprises the fixation agent and a suitable solvent, preferably water. The preferably fixed, renal tissue sample is then embedded, for example, in paraffin and cut into suitable sections. Optionally, the, preferably fixated, renal tissue sample is made transparent by tissue clearing, preferably by the use of acrylamide-based hydrogels (CLARITY) or organic solvents, for example, tetrahydrofuran, dichloromethane, dibenzyl ether (3DISCO, iDISCO). The tissue clearing can be done before or after immunostaining.

"Specific area A" preferably means an area where the glomeruli are visible with a plane view on FP. In other words, within the specific area, the capillary of the glomerulus has to be cut within the plane of the podocyte foot processes, so that the path of the filtration slit is visible (horizontal section). "Comparable area A'" means an area, which has the same size and the same orientation as described above for the specific area A, i.e. within the comparable area A', the capillary of the glomerulus has also to be cut within the plane of the podocyte foot processes, so that the path of the filtration slit is visible (horizontal section).

According to a preferred embodiment, the SD density, which is defined as the length of the SD per capillary area ($l_{SD}/A$) was calculated. Surprisingly, it was found that the calculation of the SD density could enhance and simplify the diagnostic procedure of podocyte FP effacement. Thus, the present Invention also relates to a method as described above, wherein (a) comprises a.1) determining the length of the slit diaphragm ($l_{SD}$) formed by podocyte foot processes in a specific area A in a renal tissue sample of said subject by super resolution light microscopy;

a.2) forming the slit diaphragm density $l_{SD}/A$ by division of the length of the slit diaphragm ($l_{SD}$) as determined in (a.1) by the specific area (A); and b) comparing the slit diaphragm density $l_{SD}/A$ as determined in step (a.2) with the slit diaphragm density $l_{SD}/A$ obtained in a renal tissue sample of a subject who at the time of the sampling showed no clinical symptoms of a disease associated with podocyte foot process effacement (healthy subject), wherein a deviation indicates a disease associated with podocyte foot process effacement.

The slit diaphragm density $l_{SD}/A$ of a healthy subject used in (b) comprises also a reference value of slit diaphragm density $l_{SD}/A$ obtained from more than one renal tissue sample and/or from more than one subject who at the time of the sampling showed no clinical symptoms of a disease associated with podocyte foot process effacement. The reference value represents the mean value of these data. The slit diaphragm density $l_{SD}/A$ of a healthy subject used in (b) can also be a reference value from the literature (if known).

According to a preferred embodiment, the renal tissue sample is immunostained, preferably with an immune staining system comprising i) at least a binding molecule directed against a protein selected from the group consisting of slit diaphragm proteins, slit diaphragm interacting proteins and podocyte cell contact proteins, preferable selected from the group consisting of nephrin, NEPH1, podocin, ZO-1, FAT-1, Claudin-5, CD2AP, FYN, Nck1, Nck2, CRIM1, IQGAP1, MAGI-2, MYO1C, MYO1E, TRPC6, ApoL1, NOTCH, Par3, Par6, Dynamin, Clathrin, b-arrestin, PKC, Grb2, $Ca^{2+}$-activated Channels (BK), and P-Cadherin, more preferably selected from the group consisting of nephrin, NEPH1, podocin, ZO-1, FAT-1, Claudin-5, more preferably nephrin.

ii) at least one fluorescence dye, preferably at least one fluorescence dye excitable by light in the range of 400 to 800 nm, more preferably a cyanine dye, more preferably a cyanine dye selected from the group consisting of Cy3, Cy3.5, Cy5, Cy5.5, Cy7, and Cy7.5, more preferably Cy3.

The binding molecule according to i) is selected from the group consisting of proteins and nucleic acids, preferably from the group consisting of antibody, aptamer, peptimer and nanobody (single-domain antibody), more preferably antibody.

As mentioned above, a disease associated with podocyte foot process effacement is a disease from the group of glomerulopathies, preferably selected from the group consisting of diabetic nephropathy, focal segmental glomerulosclerosis, membranous glomerulonephritis/membranous nephropathy and minimal change disease.

According to steps (a), (b) and (a.1), (a.2), (b) respectively, the length of the slit diaphragm ($l_{SD}$) formed by podocyte foot processes is determined by super resolution light microscopy, wherein "super resolution" means a resolution limit below 200 nm in the xy direction. Preferably, the super resolution light microscopy is selected from all super resolution microscopy techniques, and is more preferably structured illumination microscopy.

According to (b), a deviation in the comparison of the results of (a) and (b) indicates a disease associated with podocyte foot process effacement. Preferably, the deviation according to (b) is a decrease of the length of the slit diaphragm ($l_{SD}$) as determined in (a) compared to the length of the slit diaphragm ($l_{SD}$) of a subject who at the time of the sampling showed no clinical symptoms of a disease associated with podocyte foot process effacement or of the slit diaphragm density $l_{SD}/A$ formed in (a.2) compared to the slit diaphragm density $l_{SD}/A$ of a subject who at the time of the sampling showed no clinical symptoms of a disease associated with podocyte foot process effacement.

As outlined above, the determination of the width of the podocyte foot processes is an indicator for podocyte effacement. Thus, according to a preferred embodiment, the method as described above further comprises c) determining the width of podocyte foot processes in a specific area A in a renal tissue sample of said subject by super resolution light microscopy;

d) comparing the width of podocyte foot processes in a specific area A as determined in step c) with the width of podocyte foot processes in a comparable specific area A' in a renal tissue sample of a subject who at the time of the sampling showed no clinical symptoms of a disease associated with podocyte foot process effacement.

wherein a deviation determined in (b) and/or (d), preferably a deviation in (b) and (d), Indicates a disease associated with podocyte foot process effacement.

As mentioned above, a "deviation" determined in (b) preferably means a decrease. On the contrary, a "deviation" regarding step (d) means an increase, i.e. an increase of the width of podocyte foot processes.

The width of podocyte foot processes is determined by a standardized procedure in that the peak-to-peak distance from the SDs on both sides of the FP on the half-length of each FP was measured.

The subject, who's renal tissue sample is analysed, is a mammal, preferably selected from the group of human, mouse, rabbit, and rat, more preferably human and mouse, more preferably human.

The method is an in vitro method, i.e. the renal tissue sample is analysed in vitro and the length of the slit diaphragm ($l_{SD}$) formed by podocyte foot processes in a specific area A in the renal tissue sample and the slit diaphragm density $l_{SD}/A$ respectively are determined in vitro.

The invention represents a new method for diagnosing or pre-diagnosing a disease associated with podocyte foot process effacement in a subject or for determining the risk of a subject to develop a disease associated with podocyte foot process effacement that uses routine renal tissue samples of a subject, for example, histopathological paraffin sections, immunofluorescence staining, rapid assessment by super resolution light microscopy, preferably by SIM, and, preferably automatized, analysis of the results and determination of FP effacement.

The invention is described below in more detail, wherein MCD has been used as an exemplary glomerulopathy, i.e. disease associated with podocyte foot process effacement.

First, renal tissue samples, here histopathological paraffin sections, which were excess from routine pathologic histology were processed by either PAS staining for classical histological investigation or by staining with a specific antibody against the SD-protein nephrin, detected by a Cy3-conjugated secondary antibody.

Figure 1:
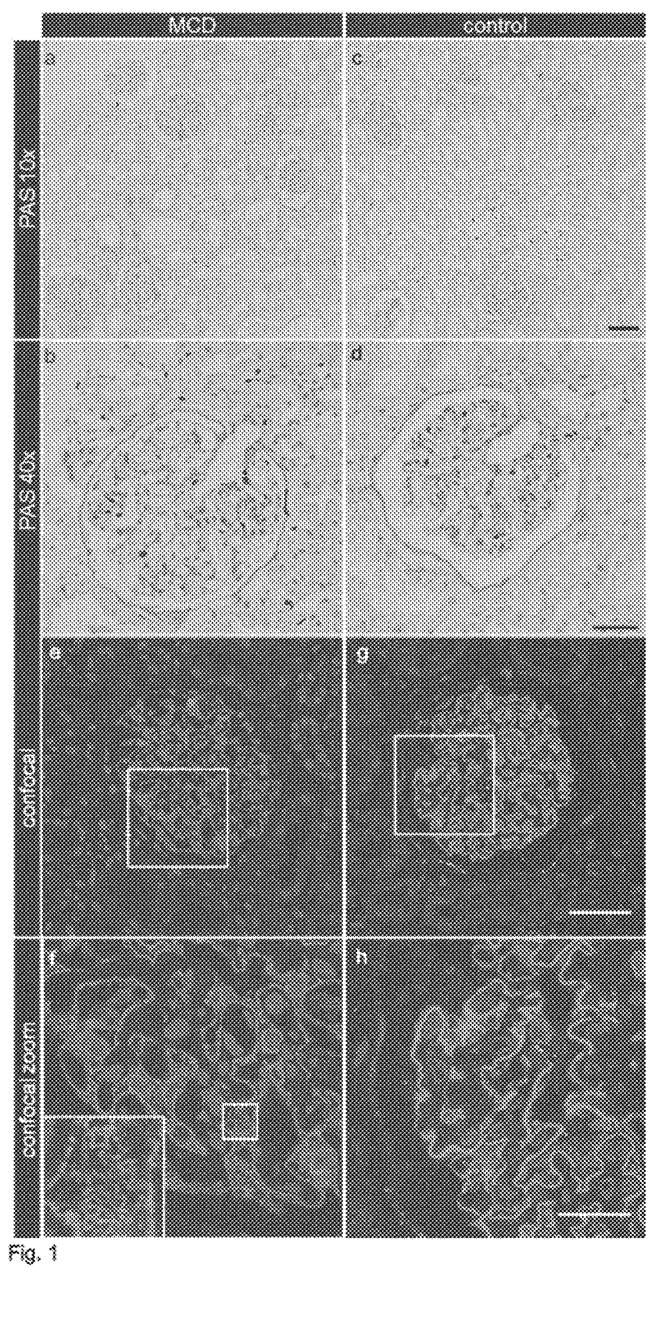
FIG. 1 shows histopathological features of the PAS-stained kidney sections originating either from MCD-diagnosed patients (a-b) or healthy control subjects (c-d). No major morphological differences between the groups could be noticed. The confocal laser scanning micrographs of nephrin-stained sections of MCD patients (e-f) or control kidneys (g-h) show a slightly weaker staining for nephrin in the MCD-diagnosed patient biopsies (e-f). The appearance of single nephrin-positive SDs can be distinguished (f, inset). The scale bars indicate in c 100 µm, in d 40 µm, in g 50 µm and in h 20 µm.

The PAS-stained sections revealed no major difference between the biopsies originating from healthy patients compared with the biopsies of MCD-diagnosed subjects (FIG. 1). Some MCD-biopsies showed a slight dilation of proximal tubules (FIG. 1a-b) and decreased staining of the brushed border of the proximal tubule cells consistent with low-grade tubular damage. All these, rather unspecific features are commonly found in biopsies which are diagnosed for MCD[1].

Confocal laser scanning micrographs of the nephrin-stained healthy kidney sections showed a classical linear staining pattern for nephrin (FIG. 1g-h), while in those of MCD-diagnosed patients, the staining was slightly weaker, less linear and more granulated (FIG. 1e-f). As shown in the inset in FIG. 1f, some areas in the glomeruli of MCD patients even allowed discrimination of the nephrin-stained SD.

Figure 2:
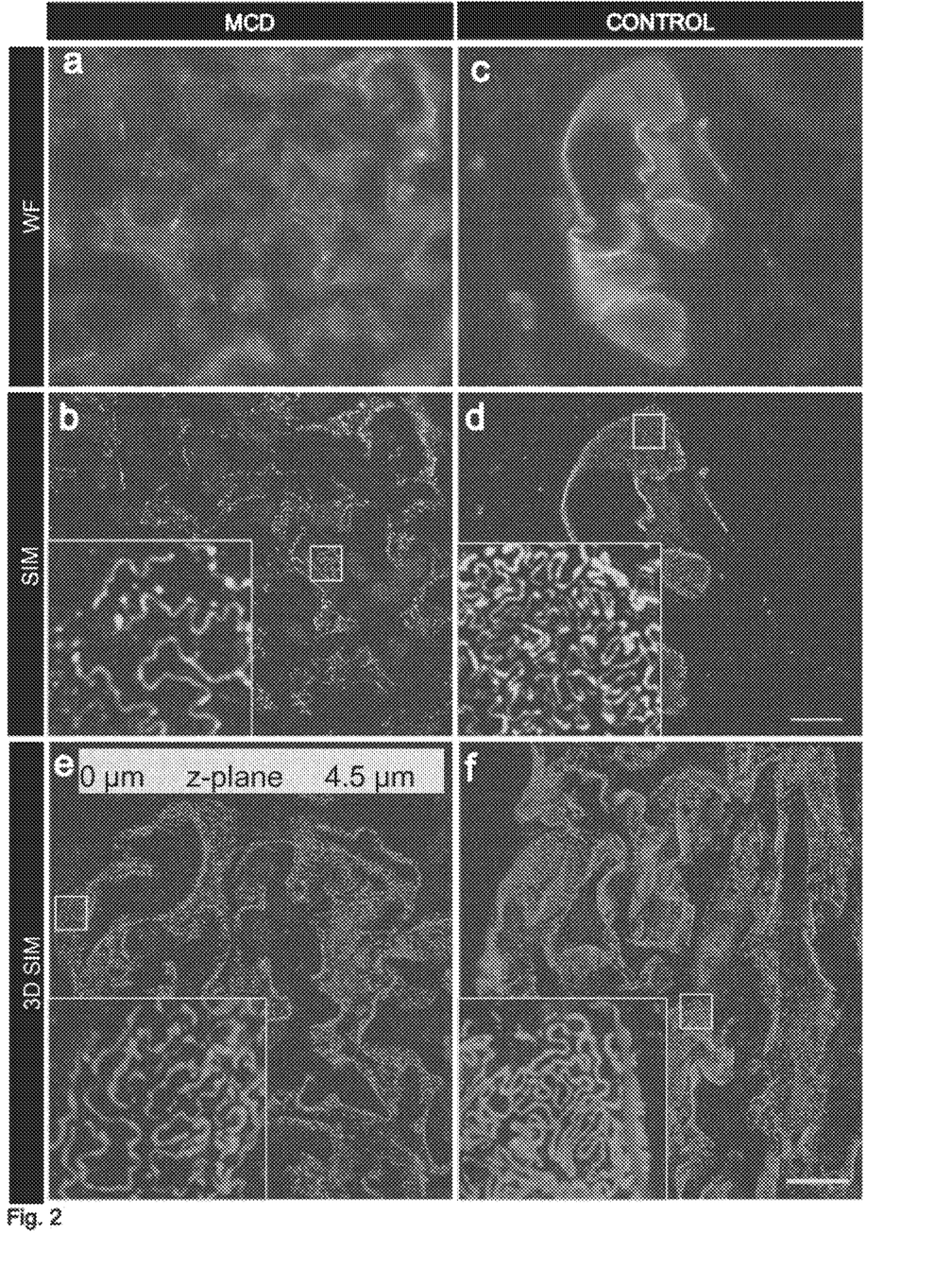

SIM z-stacks were recorded with 3 angles and 5 shifts of the grating over about 4 μm per glomerulus with a slice to slice distance of 0.3 μm. The complete volume was reconstructed as both SIM and widefield z-stacks. As shown in FIG. 2c, the widefield images showed a similar, linear staining pattern as the confocal images. The SIM reconstructions in FIGS. 2b and d showed the morphology of the SD located between single FP revealing their interdigitating morphology on the capillary. While the SIM images of the healthy control subjects showed a normal morphology with ordered FP as indicated by the meandering structure of the SD, the MCD patients showed a significantly rectilinear aspect of the SD indicating massive effacement of the podocyte FP.

Figure 3:
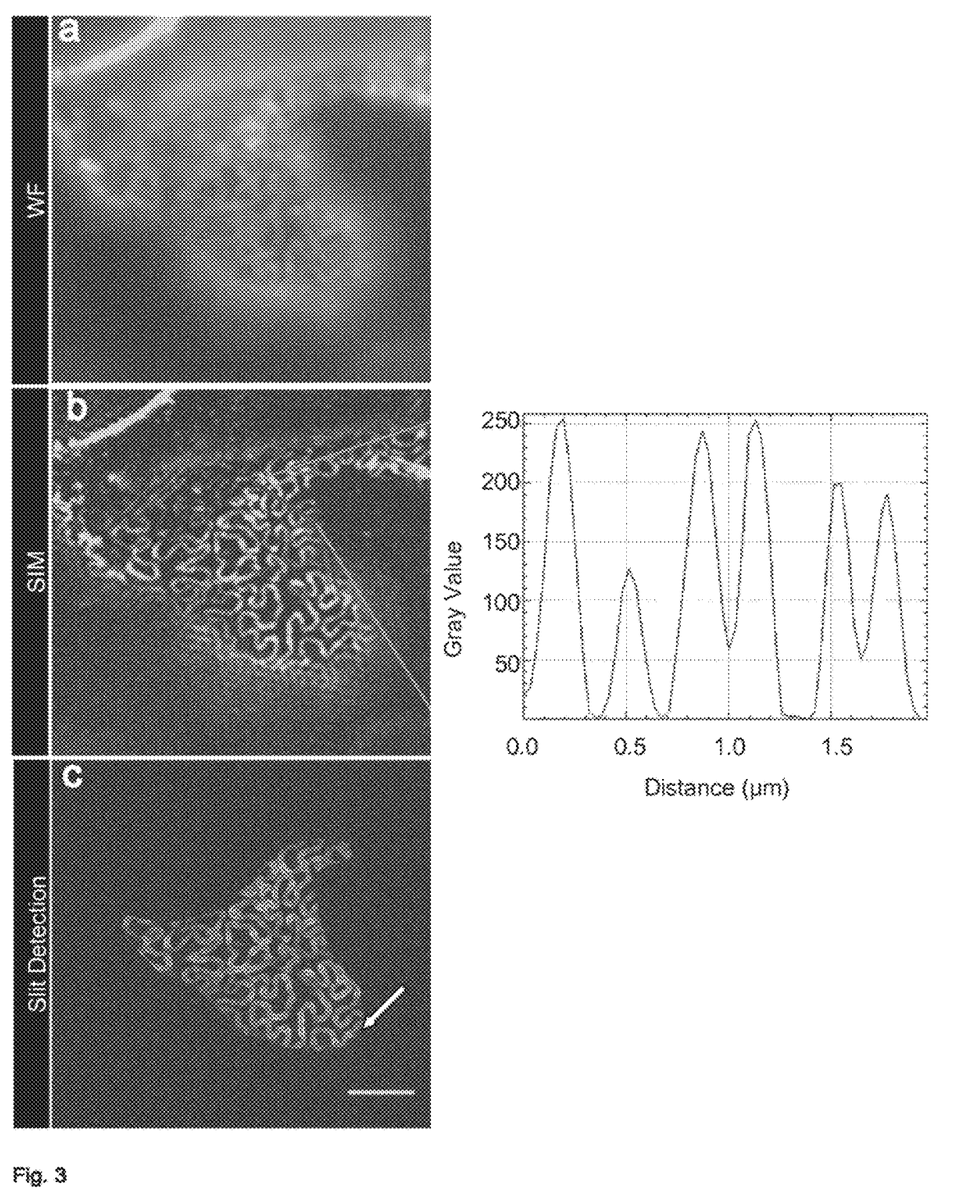

As it has long been known that the width of the effaced podocyte foot processes ($d_{FP}$) is inversely correlated with renal function in glomerular diseases like MCD[14] and membranous nephropathy[15], the $d_{FP}$ of healthy control kidneys was firstly compared with that of patients who were diagnosed for MCD. As a standardized procedure, the peak-to-peak distance from the SDs on both sides of the FP on the half-length of each FP was measured (FIG. 3b, red bar and plot). In the control group, a mean $d_{FP}$ of 0.249 μm was found (StdDev=0.068 μm, nFP=1,220, $n_{patients}$=8) compared to a significantly higher mean $d_{FP}$ of 0.675 μm (StdDev=0.256 μm, nFP=1,880, $n_{patients}$=10) in the MCD patients. The results are summarized in Table 1.

TABLE 1

| $d_{FP}$ values of MCD patients and healthy subjects (control) | | |
|---|---|---|
| $d_{FP}$ (μm) | Control | MCD |
| $M_{all\ FP}$ | 0.249 | 0.675 |
| $StdDev_{all\ FP}$ | 0.068 | 0.256 |
| $n_{FP}$ | 1,220 | 1,880 |

TABLE 1-continued $d_{FP}$ values of MCD patients and healthy subjects (control)

| $d_{FP}$ (µm) | Control | MCD |
|---|---|---|
| $M_{patients}$ | 0.249 | 0.675 |
| $StdDev_{patient}$ | 0.029 | 0.081 |
| $n_{patients}$ | 8 | 10 |
| p | — | 0.000379 |

Figure 4:
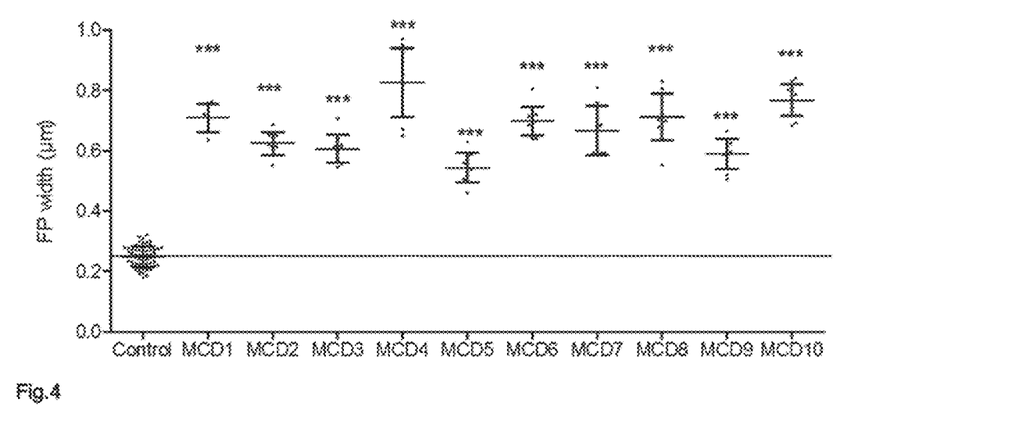
FIG. 4 shows the $d_{FP}$ for all 10 MCD patients (MCD1 to MCD10) and for the control.

As apparent, the mean $d_{FP}$ ($M_{all}$ FP) was remarkably increased in MCD subjects. Compared to control kidneys, a statistically significant difference (P<0.001) of the measured $d_{FP}$ for every MCD-diagnosed patient was found. The results for all 10 MCD patients (MCD1 to MCD10) and for the control are shown in FIG. 4.

According to an embodiment of the invention, the length of the slit diaphragm ($I_{SD}$) was measured and, according to a further embodiment, in order to optimize the image interpretation and to automatize the measurement, the SD density, which is defined as the length of the SD per capillary area ($I_{SD}/A$) was calculated. Surprisingly, it was found that the determination of the length of the slit diaphragm ($I_{SD}$) as well as the calculation of the SD density could enhance and simplify the diagnostic procedure of podocyte FP effacement.

Therefore, an ImageJ-based workflow on the popular FIJI platform[16] was established. The plugin Ridge Detection[17] was used, which automatically recognizes and segments linear structures within digital micrographs. To automatize the procedure, a specific plugin was written, which after manual selection of an area with a plane view on FP indicated by a nephrin-positive SD, automatically measured the total length of the SD and the total selected capillary area. The plugin then automatically saved the results and a picture of the segmented SD.

The $I_{SD}$ of the healthy control was determined to be 52.54 mm for an area of 16,955 µm², the mean $I_{SD}$ of the MCD patients was determined to be 30.94 mm for an area of identical size. As apparent, the length of the slit diaphragm ($I_{SD}$) in the control was remarkably larger than the length of the slit diaphragm ($I_{SD}$) in the MCD patients, i.e. the length of the slit diaphragm ($I_{SD}$) was decreased in the MCD patients.

As a baseline value of healthy control kidneys an $I_{SD}/A$ of 3.099 µm/µm² (StdDev=0.268 µm/µm², $n_{patients}$=8, $A_{total}$=16.955 µm²) was measured. Compared to that, the MCD patients showed a statistically significant smaller mean $I_{SD}/A$ of 1.825 µm/µm² (StdDev=0.493, $n_{patients}$=13, $A_{total}$=26,475 µm²).

Figure 5:
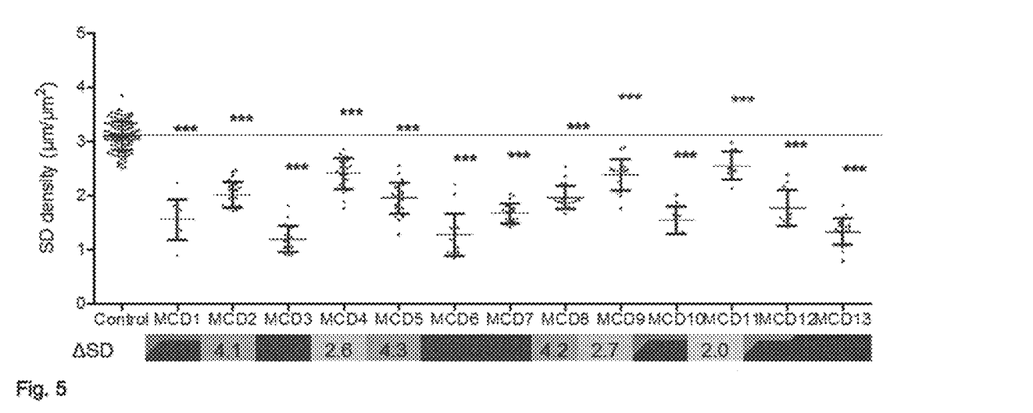
FIG. 5 shows the mean $I_{SD}/A$ for all 10 MCD patients (MCD1 to MCD10) and for the control.

As an indicator for the severity of podocyte effacement it was calculated how many standard deviations (of the control group) each MCD biopsy was below the mean of the control group. Over all MCD biopsies, a value of 4.757 standard deviations with a minimum value of 2.045 and a maximum value of 7.120 standard deviations was calculated, indicating a great variability in the severity of podocyte effacement over MCD-diagnosed patients. As shown in FIG. 5, the mean $I_{SD}/A$ of every biopsy we assessed was significantly smaller (P<0.001, $I_{SD}/A$ of all glomeruli from MCD versus control group) in comparison to the control group. The results are listed in Table 2.

TABLE 2

$I_{SD}/A$ of healthy subjects (control) versus MCD patients.

| $I_{SD}/A$ (µm/µm²) | Control | MCD |
|---|---|---|
| M | 3,099 | 1,825 |
| StdDev | 0.268 | 0.493 |
| $A_{total}$ (µm²) | 16,955 | 26,475 |
| $n_{patients}$ | 8 | 13 |
| $n_{glomeruli}$ | 72 | 128 |
| p | — | 0.000166 |
| StdDev below control | — | 4,757 |

Figure 6:
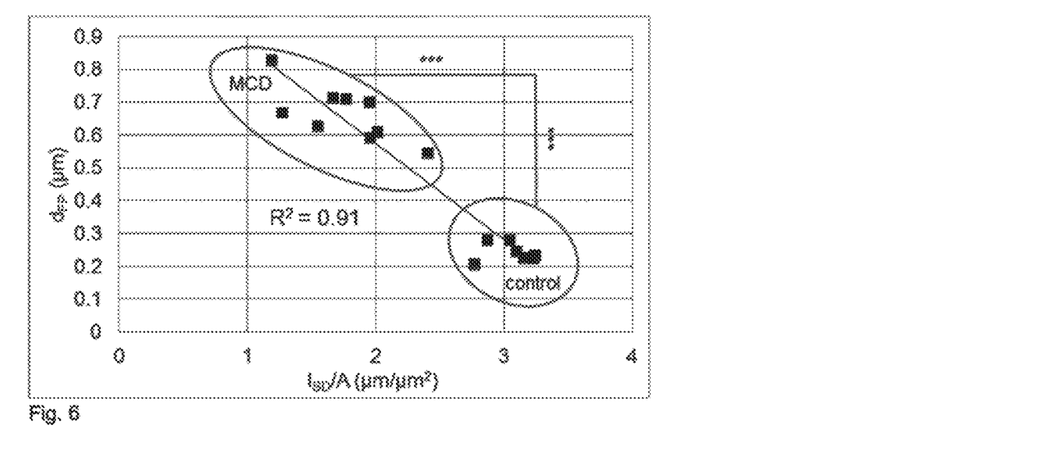
FIG. 6 shows mean values of $d_{FP}$ and $I_{SD}/A$, which were measured in biopsies of either MCD or control subjects, and which are plotted against each other for each individual. Both values show a linear relationship with a $R^2$ of 0.91. As already shown in Table 1 and 2, there is a significant difference between the MCD and the control group for both $d_{FP}$ and $I_{SD}/A$. ***P<0.001.

To verify the applicability of $I_{SD}/A$ as a diagnostic marker for podocyte effacement, a simple linear regression of the values of $d_{FP}$ and $I_{SD}/A$ of both MCD patients and control biopsies was calculated, which were measured by both strategies. As shown in the graph in FIG. 6 both values were linearly correlated ($R^2$=0.91) so it was concluded that both strategies are equivalent to diagnose podocyte FP effacement.

To summarize, the present invention presents a novel, easy and quick pathohistological approach to diagnose and quantify FP effacement in kidney biopsies. The protocol uses standard methods, which can easily be implemented in the workflow of routine diagnostics with two advantages over the state of the art methods: First, the novel approach is much faster compared to the conventional diagnosis of podocyte FP effacement by TEM. Second, trained technicians can perform the analysis of the biopsies, which reduces costs and time in the diagnostic workflow of kidney biopsies.

Another pitfall using conventional evaluation via TEM so far has been that for correct measurement of $d_{FP}$, correct orthogonal sections through the FP are required. This is not always the case and will lead to false high values for $d_{FP}$. The new technique overcomes this limitation as it utilizes plane views on the glomerular capillaries.

DESCRIPTION OF FIGURES

FIG. 2 shows micrographs of nephrin-stained glomeruli prior and after SIM reconstruction. The micrographs in a and c show a single frame of the original widefield (WF) dataset prior to SIM reconstruction. The staining pattern is linear and similar to confocal microscopy. After SIM reconstruction (b, d, maximum intensity projection of 3 subsequent frames), more details on the capillary loops can be distinguished. As shown by the magnification in d, the control kidneys show a regular staining pattern with single FP bridged by a meandering SD in between. In the MCD-diagnosed patients (b) the SD appears less meandering and the FP effaced. The images of 3D-reconstructed SIM volumes in picture e and f show the spatial aspect of the meandering SD on the capillary loops. Clearly, single FP can be distinguished on the GBM. The scale bar in a-d indicates 10 µm, the scale bar in e-f indicates 2 µm.

FIG. 3 exemplarily shows the process of automated SD detection. Panel a shows a segment of a widefield image which was SIM-reconstructed (b). As shown in the graph in panel b, $d_{FP}$ was measured as the peak-to-peak distance of neighboring SD. For an automatized approach, areas of plane capillary sections were selected and automatic SD detection was performed. The black lines within the white surrounding in panel c show the segmented SD (indicated by white arrow), the length that was measured by the FIJI plugin. The scale bar indicates 2 µm.

METHOD

1.1 Histologic Staining

Anonymized formalin-fixed and paraffin-embedded human kidney biopsies that were diagnosed for MCD by experienced pathologists of the institute of Pathology of the University Medicine Greifswald or University Erlangen-Nürnberg were used for this study. As healthy controls, anonymized excess kidney tissue of partial nephrectomies of the Department of Urology of the University Medicine Greifswald was used. The use of the biopsies from Erlangen has been approved by the Ethics Committee of the Friedrich Alexander University of Erlangen-Nürnberg, waiving the need for retrospective consent for the use of archived rest material (Ref. No. 4415). The local ethics committee of the University Medicine Greifswald approved the use of the biopsies from Greifswald. After deparaffinization in xylene and an ascending ethanol series, antigen retrieval was performed in citrate buffer by 5 minutes boiling in a pressure cooker. The slides were washed in PBS and blocked for 1 hour with 2% FBS, 2% BSA and 0.2% fish gelatin in PBS. The primary antibody (1:75 in blocking solution, polyclonal guinea pig anti-nephrin IgG, PG-N2, Progen, Heidelberg, Germany) was incubated on the slides for 4 hours at 4° C. After three times washing in PBS the secondary antibody (Cy3 conjugated goat anti-guinea pig, Jackson Immunoresearch, West Grove, Pa. USA) was incubated for 1 hour at 4° C. followed by incubation in DAPI (1:100) and threefold washing in PBS. The slides were mounted in Mowiol for Microscopy (Cart Roth, Karisruhe, Germany). For PAS staining, a standard protocol was used which can be found in the Supplemental Information.

1.2 Microscopy

Micrographs of PAS-stained sections were taken with an Olympus BX50 microscope equipped with an Olympus UC30 camera, 10× and 40× objectives were used.

For confocal laser scanning microscopy a Leica TCS SP5 (Leica Microsystems, Wetzlar, Germany) equipped with a 63× (NA 1.4) objective was used. Single micrographs of each glomerulus were acquired with 1× and 3× zoom.

For SIM a Zeiss Elyra SP.1 system (Zeiss Microscopy, Jena, Germany) equipped with a 63× (1.4 NA) oil immersion objective was used. Z-Stacks with a size of 2,430×2,430 pixels (78.35×78.35 µm) with a slice-to-slice distance of 0.3 µm were acquired over approximately 4 µm using the 561 nm laser, with 2.4% laser power and an exposure time of 100 ms. The 34 µm period grate was shifted 5 times and rotated 3 times on every frame. The 3D SIM reconstruction was performed with the Zeiss ZEN Software using following parameters: Baseline Cut, SR Frequency Weighting: 1.3; Noise Filter: −5.6; Sectioning: 96, 84, 83.

1.3 Evaluation of $d_{FP}$ and automatized $I_{SD}/A$ Measurement

The width of the $d_{FP}$ in SIM images was measured in a standardized way with FIJI: The peak-to-peak distance of two neighboring SDs was measured on the half length of a single FP. The $d_{FP}$ was evaluated for 20 FP per glomerulus, with 8-12 included glomeruli per patient leading to ~200 measurements per patient.

For automatic assessment of the SD length, a customized macro was programmed for the ImageJ-based platform FIJI and the ImageJ plugin "Ridge Detection"[16,17]. The macro only requires manual selection of a capillary area with a plane view on the SD and FP. The source code can be found in the Supplemental Information and the authors can supply the ready-to-use FIJI macro upon request.

The macro measures the total SD length ($I_{SD}$) and the capillary area (A) and saves the results to an Excel file together with a JPEG file of the result of the SD detection. To account for the SD density, $I_{SD}$ was divided by A. To check for statistical difference, the result of every biopsy was compared to the control group by Student's unpaired t-test. To check for statistical difference of the mean MCD versus control patients (Tables 1, 2), we applied a Mann-Whitney U test using SPSS (22.0 IBM SPSS Inc., Chicago, Ill., USA). To quantify the severity of the phenotype the results were expressed as "standard deviations below control".

REFERENCES

1. Fogo A B, Lusco M A, Najafian B, Alpers C E: AJKD Atlas of Renal Pathology: Minimal Change Disease. *American journal of kidney diseases the official journal of the National Kidney Foundation* 66(2): 376-7, 2015
2. Huang B, Babcock H. Zhuang X: Breaking the diffraction barrier: Super-resolution imaging of cells. *Cell* 143(7): 1047-58, 2010
3. Suleiman H. Zhang L, Roth R, Heuser J E, Miner J H, Shaw A S, Dani A: Nanoscale protein architecture of the kidney glomerular basement membrane. *eLife* 2: e01149, 2013
4. Unnersjo-Jess D. Scott L, Blom H, Brismar H: Super-resolution stimulated emission depletion imaging of slit diaphragm proteins in optically cleared kidney tissue. *Kidney Int* 89(1): 243-7, 2016
5. Gustafsson M G: Surpassing the lateral resolution limit by a factor of two using structured illumination microscopy. *J Microsc* 198(Pt 2): 82-7, 2000
6. Gustafsson M G L, Shao L, Carlton P M, Wang C J R, Golubovskaya I N, Cande W Z, Agard D A, Sedat J W: Three-dimensional resolution doubling in wide-field fluorescence microscopy by structured illumination. *Biophysical journal* 94(12): 4957-70, 2008
7. Deegens J K J, Dijkman H B P M, Borm G F, Steenbergen E J, van den Berg J G, Weening J J, Wetzels J F M: Podocyte foot process effacement as a diagnostic tool in focal segmental glomerulosclerosis. *Kidney Int* 74(12): 1568-76, 2008
8. van den Berg J G, van den Bergh Weerman M A, Assmann K J M, Weening J J, Florquin S: Podocyte foot process 9. Patrakka J, Ruotsalainen V, Ketola I, Holmberg C, Heikinheimo M, Tryggvason K, Jalanko H: Expression of nephrin in pediatric kidney diseases. *Journal of the American Society of Nephrology JASN* 12(2): 289-96, 2001
10. Furness P N, Hall L L, Shaw J A, Pringle J H: Glomerular expression of nephrin is decreased in acquired human nephrotic syndrome. *Nephrology, dialysis, transplantation official publication of the European Dialysis and Transplant Association—European Renal Association* 14(5): 1234-7, 1999
11. Agrawal V, Prasad N, Jain M, Pandey R: Reduced podocin expression in minimal change disease and focal segmental glomerulosclerosis is related to the level of proteinuria. *Clinical and experimental nephrology* 17(6): 811-8, 2013
12. Suvanto M, Jahnukainen T, Kestila M, Jalanko H: Podocyte proteins in congenital and minimal change nephrotic syndrome. *Clinical and experimental nephrology* 19(3): 481-8, 2015
13. Pullman J M, Nylk J, Campbell E C, Gunn-Moore F J, Prystowsky M B, Dholakia K: Visualization of podocyte substructure with structured illumination microscopy (SIM): A new approach to nephrotic disease. *Biomed Opt Express* 7(2): 302-11, 2016
14. Bohman S O, Jaremko G. Bohlin A B, Berg U: Foot process fusion and glomerular filtration rate in minimal change nephrotic syndrome. *Kidney Int* 25(4): 696-700, 1984
15. Hladunewich M A, Lemley K V, Blouch K L, Myers B D: Determinants of GFR depression in early membranous nephropathy. *American journal of physiology. Renal physiology* 284(5): F1014-22, 2003
16. Schindelin J, Arganda-Carreras I, Frise E, Kaynig V. Longair M. Pietzsch T, Preibisch S, Rueden C. Saalfeld S, Schmid B, Tinevez J-Y, White D J, Hartenstein V, Eliceiri K, Tomancak P, Cardona A: Fiji: An open-source platform for biological-image analysis. *Nature methods* 9(7): 676-82, 2012
17. Steger C: An unbiased detector of curvilinear structures. *IEEE Trans. Pattern Anal. Machine Intel.* 20(2): 113-25, 1998

The invention claimed is:
1. A method for diagnosing or pre-diagnosing a disease associated with podocyte foot process effacement in a subject or for determining the risk of a subject to develop a disease associated with podocyte foot process effacement, said method comprising the steps of
   a) determining the length of the slit diaphragm ($l_{SD}$) formed by podocyte foot processes in a specific area A in a renal tissue sample of said subject by super resolution light microscopy; wherein the specific area A is an area where the glomeruli are visible with a plane view on podocyte foot process;
   b) comparing the length of the slit diaphragm ($l_{SD}$) formed by podocyte foot processes in a specific area A as determined in step (a) with the length of the slit diaphragm ($l_{SD}$) formed by podocyte foot processes in a comparable specific area A' in a renal tissue sample of a subject who at the time of the sampling showed no clinical symptoms of a disease associated with podocyte foot process effacement, wherein a deviation indicates the disease associated with podocyte foot process effacement;
wherein
   the deviation according to (b) is a decrease of the length of the slit diaphragm ($l_{SD}$) as determined in (a) compared to the length of the slit diaphragm ($l_{SD}$) of a subject who at the time of the sampling showed no clinical symptoms of a disease associated with podocyte foot process effacement.
2. The method of claim 1, wherein (a) comprises
   a.1) determining the length of the slit diaphragm ($l_{SD}$) formed by podocyte foot processes in a specific area A in a renal tissue sample of said subject by super resolution light microscopy;
   a.2) forming the slit diaphragm density $l_{SD}/A$ by division of the length of the slit diaphragm ($l_{SD}$) as determined in (a.1) by the specific area (A); and
   b) comparing the slit diaphragm density $l_{SD}/A$ as determined in step (a.2) with the slit diaphragm density $l_{SD}/A$ in a renal tissue sample of a subject who at the time of the sampling showed no clinical symptoms of a disease associated with podocyte foot process effacement, wherein a deviation indicates a disease associated with podocyte foot process effacement.
3. The method of claim 1, wherein the renal tissue sample is immunostained with an immune staining system comprising
   i) at least a binding molecule directed against a protein selected from the group consisting of slit diaphragm proteins, slit diaphragm interacting proteins and podocyte cell contact proteins,
   ii) at least one fluorescence dye.
4. The method of claim 3, wherein the binding molecule according to i) is selected from the group consisting of proteins and nucleic acids.
5. The method of claim 1, wherein the disease associated with podocyte foot process effacement one or more glomerulopathies.
6. The method of claim 1, wherein the super resolution light microscopy is structured illumination microscopy.
7. The method of claim 1, wherein the deviation according to (b) further comprises a decrease of the slit diaphragm density $l_{SD}/A$ formed in (a.2) compared to the slit diaphragm density $l_{SD}/A$ of a subject who at the time of the sampling showed no clinical symptoms of a disease associated with podocyte foot process effacement.
8. The method of claim 1, further comprising
   c) determining the width of podocyte foot processes in a specific area A in a renal tissue sample of said subject by super resolution light microscopy;
   d) comparing the width of podocyte foot processes in a specific area A as determined in step c) with the width of podocyte foot processes in a comparable specific area A' in a renal tissue sample of a subject who at the time of the sampling showed no clinical symptoms of a disease associated with podocyte foot process effacement,
   wherein a deviation determined in (b) and/or (d) indicates a disease associated with podocyte foot process effacement.
9. The method of claim 8, wherein the deviation according to (d) is an increase of the width of podocyte foot processes as determined in (c) compared to the width of podocyte foot processes in a comparable specific area A' in a renal tissue sample of a subject who at the time of the sampling showed no clinical symptoms of a disease associated with podocyte foot process effacement.
10. The method of claim 1, wherein the subject is a mammal.

11. The method of claim 1, which is an in vitro method.

12. The method of claim 3, wherein the at least a binding molecule directed against a protein selected from the group consisting of slit diaphragm proteins, slit diaphragm interacting proteins and podocyte cell contact proteins, is selected from the group consisting of nephrin, NEPH1, podocin, ZO-1, FAT-1, Claudin-5, CD2AP, FYN, Nck1, Nck2, CRIM1, IQGAP1, MAGI-2, MYO1C, MYO1E, TRPC6, ApoL1, NOTCH, Par3, Par6, Dynamin, Clathrin, b-arrestin, PKC, Grb2, $Ca^{2+}$-activated Channels (BK), and P-Cadherin.

13. The method of claim 3, wherein the at least one fluorescence dye is excitable by light in the range of 400 to 800 nm.

14. The method of claim 13, wherein the at least one fluorescence dye is a cyanine dye.

15. The method of claim 14, wherein the cyanine dye is selected from the group consisting of Cy3, Cy3.5, Cy5, Cy5.5, Cy7, and Cy7.5.

16. The method of claim 15, wherein the cyanine dye is Cy3.

17. The method of claim 4, wherein the binding molecule according to i) is selected from the group consisting of antibody, aptamer, peptimer and nanobody.

18. The method of claim 17, wherein the binding molecule according to i) is an antibody.

19. The method of claim 5, wherein the disease associated with podocyte foot process effacement is selected from the group consisting of diabetic nephropathy, focal segmental glomerulosclerosis, membranous glomerulonephritis/membranous nephropathy and minimal change disease.

20. The method of claim 8, wherein a deviation determined in (b) and (d) indicates a disease associated with podocyte foot process effacement.

21. The method of claim 10, wherein the subject is selected from the group consisting of human, mouse, rabbit and rat.

22. The method of claim 21, wherein the subject is selected from the group consisting of human and mouse.

23. The method of claim 21, wherein the subject is human.

24. The method of claim 22, wherein the subject is human.

* * * * *